United States Patent
Hjorth et al.

(10) Patent No.: US 11,382,788 B2
(45) Date of Patent: Jul. 12, 2022

(54) FEMALE URINATION AID

(71) Applicant: RH Medical Design Company, LLC, Millsboro, DE (US)

(72) Inventors: Rebecca Hjorth, Millsboro, DE (US); Aric Pahnke, Toronto (CA); Joshua Sybrowsky, Lincoln, CA (US)

(73) Assignee: RH Medical Design Company, LLC, Millsboro, DE (US)

( * ) Notice: Subject to any disclaimer, the term of this patent is extended or adjusted under 35 U.S.C. 154(b) by 462 days.

(21) Appl. No.: 15/968,422

(22) Filed: May 1, 2018

(65) Prior Publication Data

US 2018/0311069 A1 Nov. 1, 2018

Related U.S. Application Data

(60) Provisional application No. 62/492,689, filed on May 1, 2017.

(51) Int. Cl.
*A61F 5/455* (2006.01)
*A61F 5/44* (2006.01)

(52) U.S. Cl.
CPC .......... *A61F 5/4553* (2013.01); *A61F 5/4556* (2013.01); *A61F 2005/4402* (2013.01)

(58) Field of Classification Search
CPC .................. A61F 5/4553; A61F 5/455–4556
See application file for complete search history.

(56) References Cited

U.S. PATENT DOCUMENTS

| | | | |
|---|---|---|---|
| 4,608,046 A * | 8/1986 | Towfigh | A61F 5/4556 4/144.3 |
| 4,937,890 A | 7/1990 | Tafur | |
| 4,986,823 A * | 1/1991 | Anderson | A61F 5/455 604/329 |
| 5,893,176 A | 4/1999 | Magiera et al. | |
| 5,966,748 A | 10/1999 | Young et al. | |
| 6,547,771 B2 | 4/2003 | Robertson et al. | |
| D579,556 S | 10/2008 | Stebler | |
| D674,087 S | 1/2013 | Linton | |
| 8,945,077 B2 | 2/2015 | Valenti | |
| 2004/0181862 A1* | 9/2004 | Brummer | A61F 5/4556 4/144.4 |
| 2007/0006368 A1 | 1/2007 | Key | |
| 2010/0331798 A1* | 12/2010 | Block | A61F 5/4556 604/329 |
| 2011/0030130 A1* | 2/2011 | Stein | A61F 5/4556 4/144.2 |
| 2012/0117720 A1* | 5/2012 | King-Boutte | A61F 5/4556 4/144.2 |
| 2013/0239311 A1* | 9/2013 | Valenti | A61F 5/4556 4/144.3 |
| 2015/0223967 A1* | 8/2015 | Rojals Fort | A61F 5/4556 4/144.2 |

\* cited by examiner

*Primary Examiner* — Tatyana Zalukaeva
*Assistant Examiner* — Meagan Ngo
(74) *Attorney, Agent, or Firm* — Goodhue, Coleman & Owens, P.C.

(57) ABSTRACT

A female urination aid and method of use. The female urination aid includes a lip shaped to fit against a vagina of the user. The lip is rounded for the comfort of the user. The lip defines an opening. The female urination aid further includes a nub extending from a first end of the lip. The nub is rounded. The female urination aid further includes a body extending from a bottom portion of the lip. The body defines a channel for shunting urine away from the user. A bottom of the body defines an outlet.

21 Claims, 5 Drawing Sheets

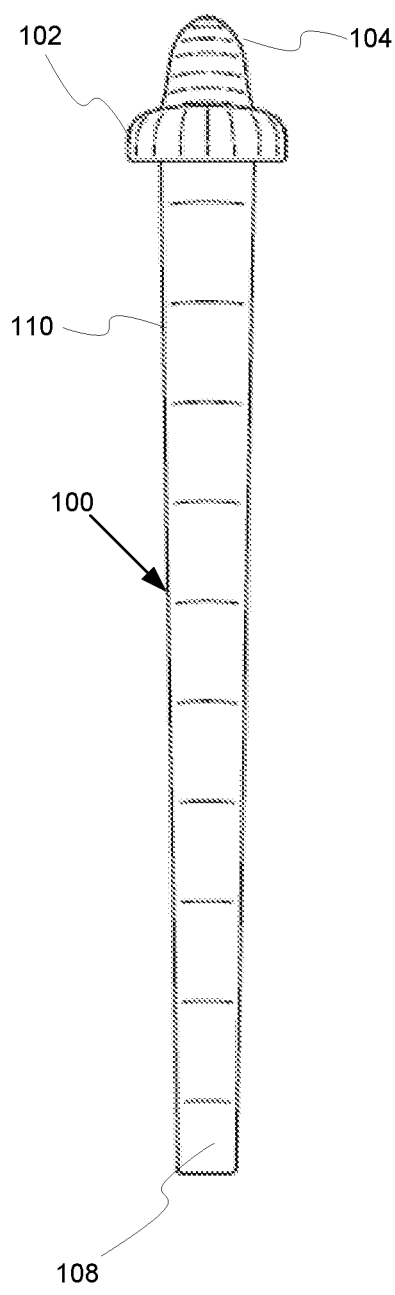
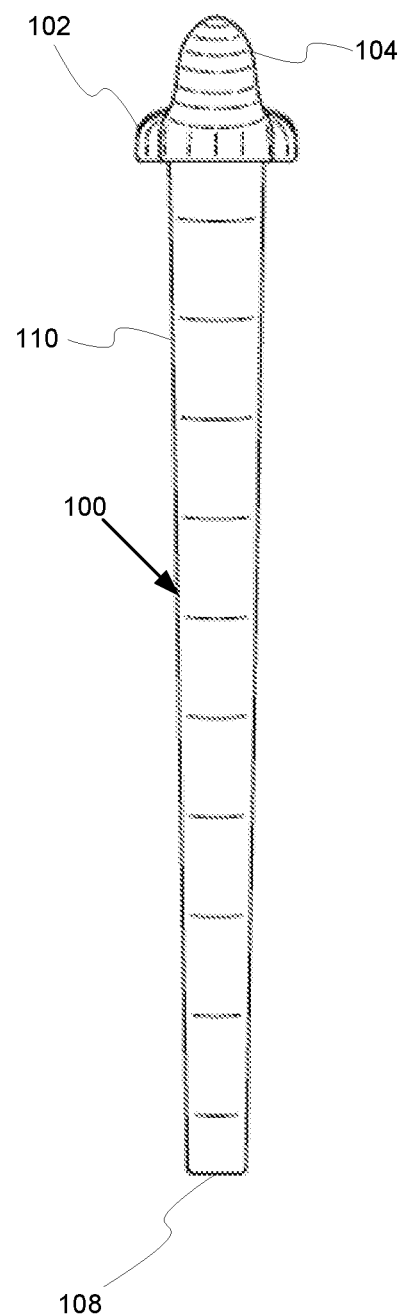
FIG. 4A
FIG. 4B

FEMALE URINATION AID

PRIORITY STATEMENT

This application claims priority to U.S. Provisional Patent Application 62/492,689, filed on May 1, 2017, and entitled Female Urination Aid, hereby incorporated by reference in its entirety.

BACKGROUND

I. Field of the Disclosure

The illustrative embodiments relate to a female urination aid. More specifically, but not exclusively, the illustrative embodiments relate to a system, method, and female urination aid for facilitating women that may have various medical conditions.

II. Description of the Art

Millions of women throughout the world suffer from vaginal issues, such as vaginal tearing, genital herpes, bacterial vaginosis, difficult births, and vaginally atrophy. For example, approximately 1 in 5 of every women between ages 14-49 suffer from genital herpes. Women with these conditions and symptoms may experience excruciating pain when urinating or at a minimum discomfort. An average person urinates between four and ten times a day. As a result, females with urinary pain or discomfort based on vaginal issues may dread using the bathroom throughout the day, which may cause additional emotional and physical trauma.

SUMMARY OF THE DISCLOSURE

The illustrative embodiments provide a female urination aid, system, and method for utilizing the female urination aid. One embodiment provides a female urination aid and method of use. The female urination aid includes a lip shaped to fit against a vagina of the user. The lip is rounded for the comfort of the user. The lip defines an opening. The female urination aid further includes a nub extending from a first end of the lip. The nub is rounded. The female urination aid further includes a body extending from a bottom portion of the lip. The body defines a channel for shunting urine away from the user. A bottom of the body defines an outlet.

Another embodiment provides a method of utilizing a female urination aid. A female urination aid is removed from a container. The female urination aid is positioned against a vulval vestibule of the user for urination. A lip of the female urination aid fits inside the labia minor of the vagina of the user and forms a tight seal around a urethral meatus of the user. A nub extending from the lip interfaces with the vagina of the user.

BRIEF DESCRIPTION OF THE DRAWINGS

Illustrated embodiments of the illustrative embodiments are described in detail below with reference to the attached drawing figures, which are incorporated by reference herein, and where:

FIGS. 4A-4B are side views of the female urination aid of FIG. 1 in accordance with an illustrative embodiment.

DETAILED DESCRIPTION OF THE DISCLOSURE

Figure 1:
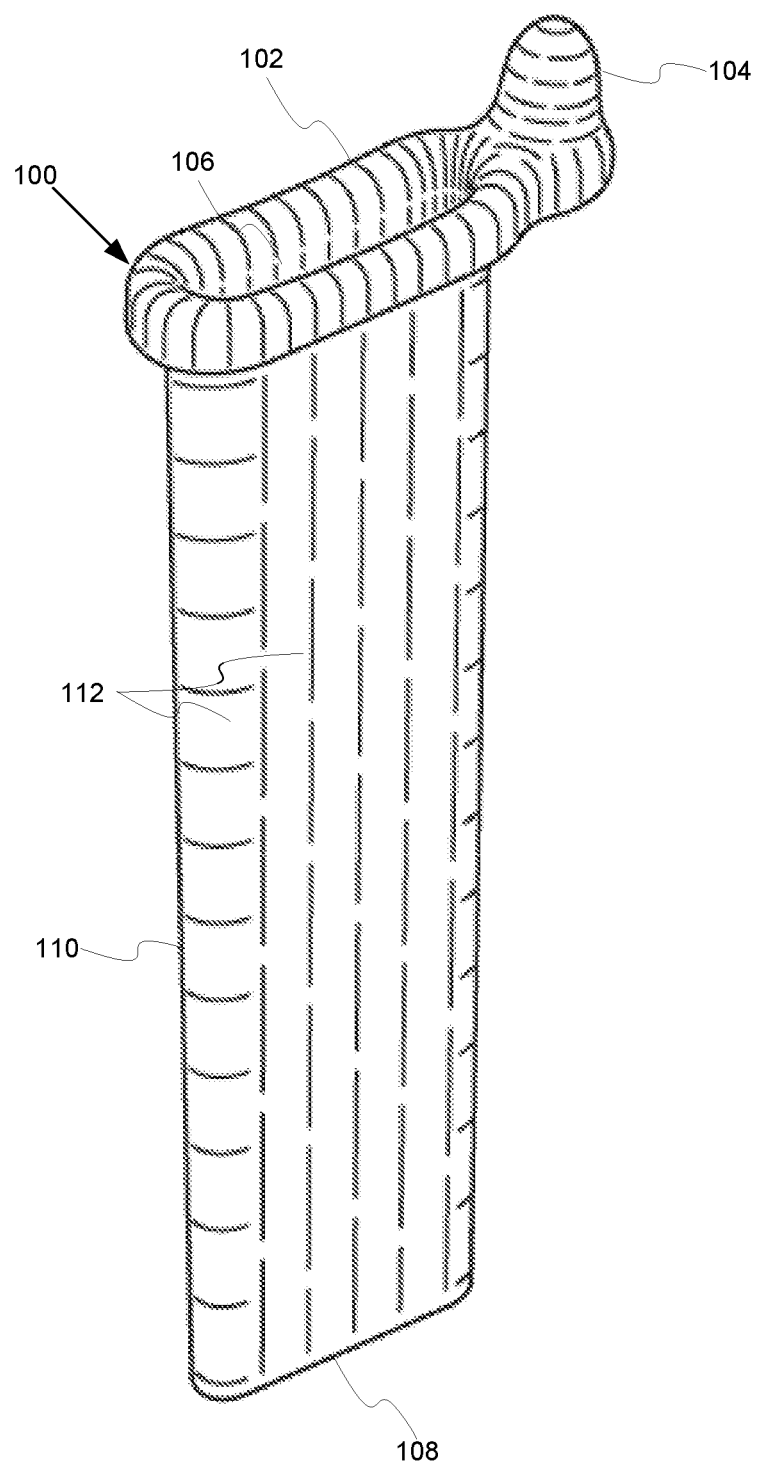
FIG. 1 is a pictorial representation of a female urination aid in accordance with an illustrative embodiment.
Figure 2:
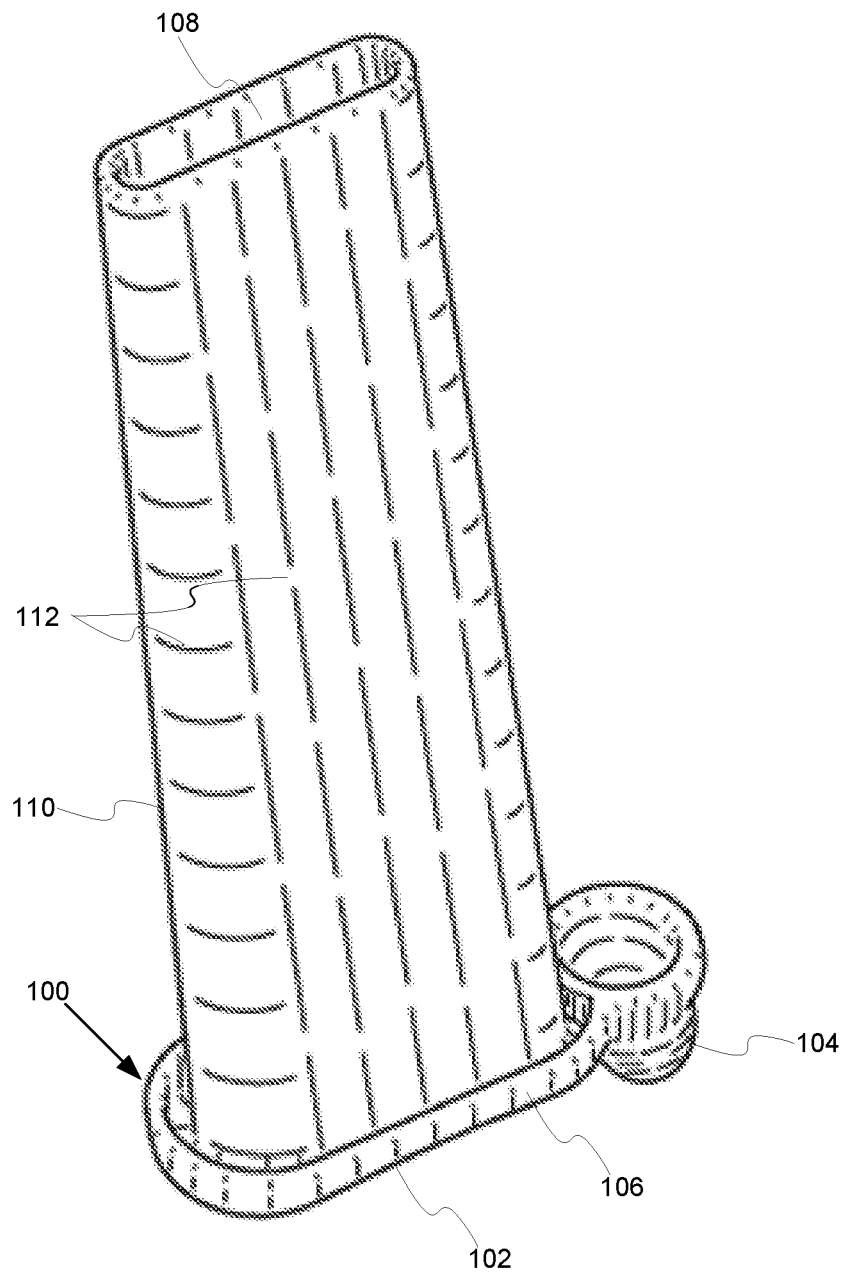
FIG. 2 is a bottom perspective view of the female urination aid of FIG. 1 in accordance with an illustrative embodiment.
Figure 3:
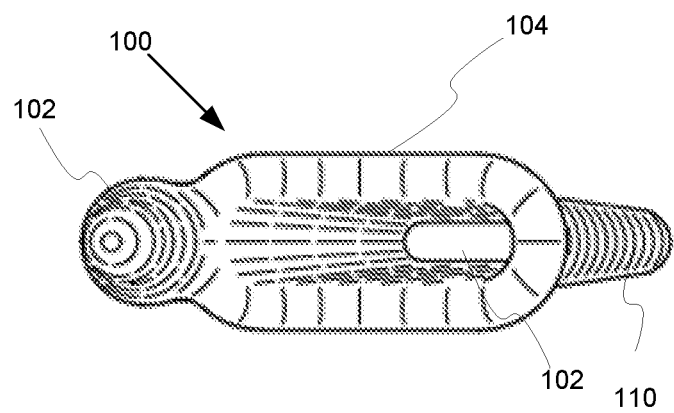
FIG. 3 is a top view of the female urination aid of FIG. 1 in accordance with an illustrative embodiment.
Figure 3:
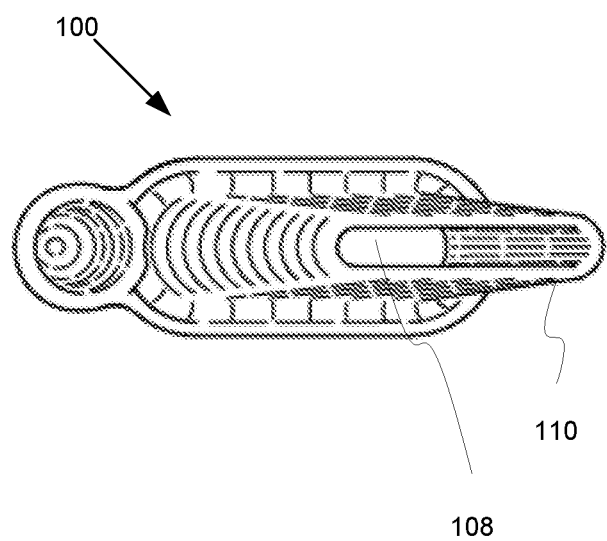

The illustrative embodiments provide a female urination aid, system, device, apparatus, and method of use thereof. In one embodiment, the female urination aid is a disposable device that funnels urine away from the vagina of a female user thereby minimizing contact of the area and with sores, inflamed tissues, wounds, or other areas of soreness. The illustrative embodiments may be particularly useful for women suffering from vaginal tearing, genital herpes (or other sexually transmitted diseases), bacterial vaginosis, vaginal atrophy, or do any number of other sicknesses, diseases, infections, or so forth. For example, the female urination aid may be particularly useful for females that have recently delivered a baby or experienced other traumatic events.

The female urination aid is a handheld device that shields the hand of the user from urine. Similarly, the placement of the female urination aid within the vagina bypasses wounds, tears, or sores in or around the female genitalia and urethra. Likewise, the female urination aid shunts urine away from the vulva. In one embodiment, the female urination aid is disposable, flushable, and biodegradable the female urination aid may be configured to interface with the vulval vestibule.

The female urination aid is unique in that it provides a small and comfortable indicator (a nub) for proper placement of the lip and the female urination aid during urination. In one embodiment, the nub is utilized as a "vaginal locator." First the user locates her vaginal with the nub and then slightly inserts the lip towards the vulval vestibule and labia minor thus create a right seal around the urethral meatus utilizing the lip. The female urination aid may be inserted slightly into the vaginally opening for proper positioning as herein described. The female urination aid includes a narrow opening that may be expanded by squeezing the narrow edges. The size and shape of the narrow opening may be expanded as needed to best fit the physiology, geometry, and physical needs of the user. In one embodiment, the female urination aid may include grips for the user to securely hold or grasp during urination. In other embodiments, the female urination aid may be expandable or curved to direct the urine into a receptacle, such as a toilet or urinal, or to otherwise channel the urine away from the body of the user. The female urination aid may be sized, shaped, and curved in any number of directions.

The female urination aid may be formed from any number plastics, polymers, metals, papers, or a combination of materials. The size of the female urination aid may be sized for any number of users including children, adolescents, teenagers, and women of all ages and body types. In one embodiment, the female urination aid may interface with the body of the user at the urethral orifice. The female urination aid may be adjusted or modified by the user squeezing or otherwise adjusting the shape and/or size of the female urination aid to fit the physiology and other needs of the user.

One embodiment provides a female urination aid and method of use. The female urination aid includes a lip shaped to fit against a vagina of the user. The lip is rounded for the comfort of the user. The lip may be a thin oval that is slightly more squared. The lip defines an opening for receiving urine. The female urination aid further includes a nub extending from a first end of the lip. The nub is rounded. The female urination aid further includes a body extending from a bottom portion of the lip. The body of the channel is narrower than the lip. The body defines a channel for shunting urine away from the user. A bottom of the body defines an outlet.

Another embodiment provides a method of utilizing a female urination aid. A female urination aid is removed from a container. The female urination aid is positioned against a vulval vestibule of the user for urination. A lip of the female urination aid fits inside the labia minor of the vagina of the user and forms a tight seal around a urethral meatus of the user. A nub extending from the lip interfaces with the vagina of the user.

The body of the female urination aid may define one or more channels as described herein. The outer surface (that comes in contact with the skin or tissues of the user) of the body and female urination aid may utilize a first material (non-slip, antimicrobial, antibacterial, etc.) while the interior surface (does not contact the body of the user, only bodily fluids) of the body and female urination aid may utilize a second material (e.g., non-absorbing, cheaper, etc.). In one embodiment, the female urination aid may be formed from cardboard, paper, plastic, or any number of other materials that may be easily recycled or environmentally friendly. The lip, top edge/end, or application portion of the female urination aid may be rounded and ergonomic to fit the body of the user. The lip and the nub may be hollowed or thin materials to minimize material usage as well as waste.

The female urination aid may be coated with any number of anti-bacterial, anti-microbial, anesthetic, or other coatings, materials, or layers. Alternatively, the female urination aid may be coated with one or more medications, agents, probiotics, moisturizers, sanitizers, topical treatment materials (e.g., lotion, powder, capsules, etc.), or so forth. For example, a numbing agent and antibiotics may be deposited on the lip and nub for delivery to the patient during usage of the female urination aid. The materials may be a fine coating, integrated in the material of the female urination aid, lines, dots, or other patterns of materials, or so forth.

The female urination aid may be sized differently for different ages, sizes, and types of users (e.g., ailments, conditions, diseases, etc.). In some embodiments, the female urination aid may be manufactured and sealed so as to comply with FDA, medical, industry, or other applicable protocols, requirements, standards, processes, and laws. The female urination aid may be molded, printed, or manufactured utilizing any number of combination of processes.

Turning now to FIGS. 1-5 illustrating various views of the female urination aid 100. In one embodiment, the female urination aid 100 may include a lip 102, a nub 104, an opening 106, an outlet 108, a body 110, and grips 112. The components of the female urination aid 100 may further define a channel 114. The channel 114 is an conduit for conducting the urine from the opening 106 to the outlet 108. Many portions of the female urination aid 100 are smooth and low friction allowing for easy and pain-free placement of the female urination aid within and adjacent the corresponding position of the user's body.

In one embodiment, the female urination aid 100 is a small disposable device that funnels or shunts urine away from the vagina to minimize urinary contact with sores, tissue, or skin. For example, the user may suffer from sores on the labia minora of the user's vagina. In one embodiment, the lip 102 is a substantially oval-shaped toroid. The lip 102 is rounded to comfortably fit or rest against the urethral and vaginal openings of the user during urination. The lip 102 defines the opening 106 of the channel 114. The opening 106 is positioned against the vagina of the user. The opening 106 receives the urine and other fluids to shunt them away from the body of the user through the channel 114 to a toilet or other selected disposal area or device. In one embodiment, the female urination aid 102 is flexible enough to allow the opening 106 to be expanded or contracted as needed. In one example, the opening 106 may be approximately seven millimeters (7 mm) wide by default, but when the female urination aid 100 is squeezed along the narrow edges may expand to one centimeter (1 cm). Deformation of the female urination aid 100 during utilization is not only possible, but expected.

The advantage of the female urination aid 100 being flexible is that women wish to prevent urinating on their hand when using the female urination aid 100. Each user may squeeze the female urination aid 100 to adapt the opening 106 to their own physiology. For example, a narrower opening may be more beneficial for women with genital herpes whereas menopausal women may not need that same level of protection because of their respective pain levels.

A backend of the lip 102 extends (upward) away from the body 110 to form the nub 104. The nub 104 may align with or extend from the edges of the lip 102. The nub 104 is a rounded protrusion or extension from the backend of the lip 102. In one embodiment, the nub 104 has a bell shape that integrates with the lip 102. The female urination aid 100 is unique in that it provides a small and comfortable indicator (the nub 104) regarding proper placement of the lip 102 and the female urination aid 100 overall. In one embodiment, the nub is utilized as a "vaginal locator." First the user locates her vaginal with the nub and then slightly inserts the lip 102 towards the vulval vestibule and labia minor thus create a seal around the urethral meatus.

The grips 112 allow the user to hold and manipulate the female urination aid 100. In one embodiment, the grips 112 may represent miniature protrusions, ridges, indentations, divots, or patterns on the body 110 of the female urination aid 100 (whether protruding or within the body 110). The grips 112 may extend horizontally or longitudinally on the body 110. The grips 112 may also be integrated as part of the lip 102. For example, the grips 112 may be created during a manufacturing process, such as molding. In other embodiments, the grips 112 may extend to the lip 102 and the nub 104. The grips 112 may also represent any number of stickers, adhesives, bands, wraps, or so forth that may be attached to the female urination aid 100. In one embodiment, the grips 112 may also be decorative thereby making the female urination aid 100 more aesthetically pleasing to girls and women that may benefit from using it. For example, the branding, trademarks, or other applicable information may be on the body 110 of the female urination aid 100.

Although not shown, the female urination aid 100 may define any number of channels, lumens, rifling or twists, or other components/structures for best conducting the urine from the opening 106 to the outlet 108 of the channel 114. In one embodiment, the body 110 may curve forward or rearward from the front of the female urination aid 100 (opposite the nub 104). The curvature of the body 110 and correspondingly the channel 114 may be utilized to better shunt the urine away from the user during utilization of the female urination aid and 100. In other embodiments, the length of the body 110 and the associated channel 114 may be slightly or significantly extended to further channel the urine away from the body of the user. The size and shape of the lip 102, the nub 104, and the opening 106 may vary to better fit individuals with different vagina and body sizes and shapes. In one embodiment, the female urination aid 100 may represent two parts that may be interconnected. The body 110 of the female urination aid 100 may telescope out so that it fits into smaller spaces. The female urination aid 100 may collapse and telescope as needed. For example, segments of the body 110 may be incrementally sized or utilize layers, lips, or fasteners as are known in the art.

The size of the female urination aid 100 may also be varied for differently sized and shape of users (e.g., length of the body 110, width of the lip 102 and body 110, height and diameter of the nub 104, etc.). The female urination aid 100 may be utilized in any number of circumstances. For example, the female urination aid may be utilized while standing, sitting, or other positions above or on a toilet, urinal, or other waste receptacle. The female urination aid 100 may also be utilized in locations, circumstances, or environments where a traditional toilet or human waste disposal system is not available. Although not shown, the illustrative embodiments may be utilized for other purposes, bodily functions, and fluids.

Figure 5:
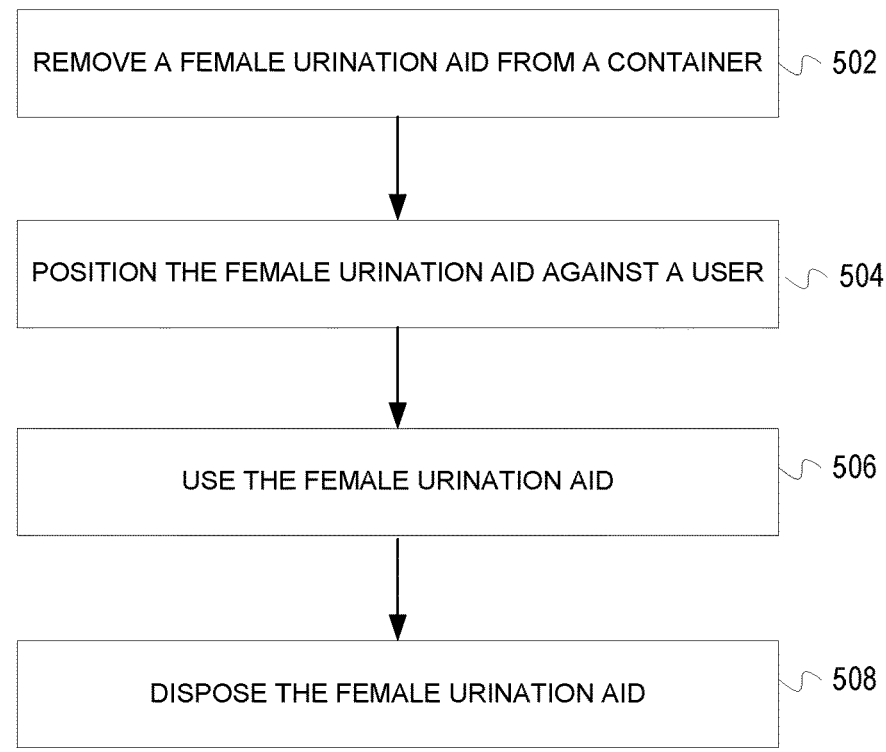
FIG. 5 is a flowchart of a process for utilizing a female urination aid in accordance with an illustrative embodiment.

FIG. 5 is a flowchart of a process for utilizing a female urination aid in accordance with an illustrative embodiment. The process of FIG. 5 may be implemented utilizing a female urination aid. A female utilizing the female urination aid may be suffering from any number of conditions or circumstances that encourage utilization of the female urination aid.

The process may begin by removing a female urination aid from a container (step 502). In one embodiment, the container may be a disposable plastic or paper wrap. During manufacturing, the female urination aid may have been sealed in any number of containers, bags, cases, wrappers, or so forth. The female urination aid may be secured and stored individually or in a group. The female urination aid may be removed through a zipper, perforation, ripped, punctured, or otherwise removed from the container. In other embodiments, the female urination aid may be expanded to fit the body shape, size, and configuration of the user. For example, the lips of the female urination aid may deform to fit within the labia minor and form a tight seal around the urethral meatus.

Next, the female urination aid is positioned against the user (step 504). In one embodiment, a rounded lip of the female urination aid comfortably fits against the urethral and vaginal openings of the vagina of the user to aid in shunting urine away from the body. The female urination aid is unique in that it provides a small and comfortable indicator (the nub) regarding proper placement of the lip and the female urination aid overall. In one embodiment, the nub is utilized as a "vaginal locator." First the user locates her vaginal with the nub and then slightly inserts the lip towards the vulval vestibule and labia minor thus creating a seal around the urethral meatus.

In another embodiment, the user may squeeze or otherwise deform or modify the shape of the female urination aid (including the lip and opening) to change fluid flow properties as well the fit. The shape of the female urination aid may be modified during usage to best fit the physiology of the user (e.g., vagina size and shape) and the issues the user may be facing (e.g., sores, disease, etc.).

Next, the female urination aid is disposed (step 506). In one example, the female urination aid may be disposed in a waste basket, garbage, or other container. In some embodiments, the female urination aid may be configured to be recycled. The female urination aids may also be composted, mulched, or otherwise processed. In another embodiment, the female urination aid may dissolve in water and may thus be flushed after usage. In other embodiments, the female urination aid may be composed of any number of materials that may be washed, disinfected, sanitized, or otherwise cleaned for multiple uses (e.g., metals, medical grade plastics, etc.).

The illustrative embodiments is not to be limited to the particular embodiments described herein. In particular, the illustrative embodiments contemplates numerous variations in the type of ways in which embodiments may be applied to female urination aids. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the illustrative embodiments. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments and is not intended to be limiting in scope. The following claims set forth a number of the embodiments disclosed with greater particularity.

What is claimed is:

1. A female urination aid, comprising:
   a lip shaped to fit against a vagina of a user, wherein the lip is rounded for comfort of the user, and wherein the lip defines an opening;
   a nub extending perpendicularly from a first end of the lip, wherein the nub consists of a single bell shaped structure that has a rounded shape configured to fit against the user and an open end opposite the rounded shape configured to face away from the user during use;
   a body extending from a bottom portion of the lip, wherein the body defines a channel for shunting urine away from the user, and wherein a bottom of the body defines an outlet.

2. The female urination aid of claim 1, wherein the lip is a substantially oval-shaped toroid.

3. The female urination aid of claim 1, wherein the lip and the nub are configured to fit against urethral and vaginal openings of the user, and wherein the nub extends upward perpendicularly to a plane of the lip.

4. The female urination aid of claim 1, wherein an exterior portion of the body defines grips for the user to hold the female urination aid.

5. The female urination aid of claim 1, wherein the channel defines ridges for guiding the urine through the female urination aid.

6. The female urination aid of claim 1, wherein the lip is configured to fit inside labia minor of the vagina and forms a tight seal around a urethral meatus of the user.

7. The female urination aid of claim 1, wherein the female urination aid is formed from a single piece of plastic.

8. The female urination aid of claim 1, wherein the female urination aid is collapsible to close the opening when not in use.

9. The female urination of claim 1, wherein the body defines grips for the user to securely grip the body during utilization.

10. The female urination aid of claim 1, wherein the female urination aid is biodegradable.

11. The female urination aid of claim 1, wherein the female urination aid is water soluble.

12. The female urination aid of claim 1, wherein a bottom portion of the body is curved to further shunt the urine away from the body of the user.

13. The female urination aid of claim 1, wherein the female urination aid shunts the urine away from the user without getting urine on hands or body of the user.

14. A method of utilizing a female urination aid, comprising:
    removing the female urination aid from a container;
    positioning the female urination aid against a vulval vestibule of a user for urination, wherein a lip of the female urination aid fits inside labia minor of the vagina of the user and forms a tight seal around a urethral meatus of the user, wherein a nub defining a singular bell shaped structure extends from one end of the lip for comfortable positioning of the female urination aid, and wherein a rounded surface of the singular bell shaped structure of the nub extends perpendicularly from a plane of the lip interfaces with the vagina of the user and an open end opposite the rounded surface is configured to face away from the user during use.

15. The method of claim 14, wherein the lip and the nub are substantially rounded for comfort of the user.

16. The method of claim 14, further comprising:
    shunting urine through a channel of the female urination aid without the urine contacting the user.

17. The method of claim 16, wherein the female urination aid shunts the urine away from a body of the user.

18. The method of claim 14, further comprising:
    disposing of the female urination aid.

19. The method of claim 14, wherein the female urination aid is secured for positioning utilizing grips disposed on an exterior of a body of the female urination aid.

20. The method of claim 14, wherein the nub ensures proper placement of the female urination aid.

21. The method of claim 14, further comprising:
    expanding an opening of the female urination aid to fit the user.

* * * * *